(12) United States Patent
Tang (10) Patent No.: US 8,688,760 B2
(45) Date of Patent: Apr. 1, 2014

(54) DETERMINING POPULATION BOUNDARIES USING RADIAL DENSITY HISTOGRAMS

(75) Inventor: Mengxiang Tang, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 563 days.

(21) Appl. No.: 13/025,127

(22) Filed: Feb. 10, 2011

(65) Prior Publication Data

US 2012/0036175 A1  Feb. 9, 2012

Related U.S. Application Data

(60) Provisional application No. 61/305,940, filed on Feb. 18, 2010.

(51) Int. Cl.
*G06F 17/15* (2006.01)
(52) U.S. Cl.
USPC ............................................. 708/424

(58) Field of Classification Search
USPC ........................................................ 708/424
See application file for complete search history.

(56) References Cited

U.S. PATENT DOCUMENTS

| | | | |
|---|---|---|---|
| 5,408,307 A | 4/1995 | Yamamoto et al. | |
| 5,627,040 A | 5/1997 | Bierre et al. | |
| 6,014,904 A | 1/2000 | Lock | |
| 6,944,338 B2 | 9/2005 | Lock et al. | |
| 8,031,423 B1 * | 10/2011 | Tsai et al. | 360/48 |
| 8,224,425 B2 * | 7/2012 | Freeman et al. | 600/473 |
| 2002/0064233 A1 * | 5/2002 | Terreault et al. | 375/261 |

FOREIGN PATENT DOCUMENTS

EP  0 633 462  1/1995

* cited by examiner

*Primary Examiner* — Tan V. Mai
(74) *Attorney, Agent, or Firm* — Knobbe Martens Olson & Bear LLP (57) ABSTRACT

Apparatuses and methods for determining population boundaries are described. In one embodiment, population boundaries are determined using radial density histograms.

5 Claims, 9 Drawing Sheets

DETERMINING POPULATION BOUNDARIES USING RADIAL DENSITY HISTOGRAMS

BACKGROUND OF THE INVENTION

1. Field of the Invention

The present invention relates generally to methods for locating clusters in multidimensional data. The present invention is particularly applicable to identifying clusters corresponding to populations of cells or particles in data generated by cytometry, more particularly, flow cytometers.

2. Description of Related Art

Particle analyzers, such as flow and scanning cytometers, are well known analytical tools that enable the characterization of particles on the basis of optical parameters such as light scatter and fluorescence. In a flow cytometer, for example, particles, such as molecules, analyte-bound beads, or individual cells, in a fluid suspension are passed by a detection region in which the particles are exposed to an excitation light, typically from one or more lasers, and the light scattering and fluorescence properties of the particles are measured. Particles or components thereof typically are labeled with fluorescent dyes to facilitate detection, and a multiplicity of different particles or components may be simultaneously detected by using spectrally distinct fluorescent dyes to label the different particles or components. Typically, a multiplicity of photodetectors, one for each of the scatter parameters to be measured, and one for each of the distinct dyes to be detected. The data obtained comprise the signals measured for each of the light scatter parameters and the fluorescence emissions.

Cytometers further comprise means for recording the measured data and analyzing the data. For example, typically, data storage and analysis is carried out using a computer connected the detection electronics. The data typically are stored in tabular form, wherein each row corresponds to a the data for one particle, and the columns correspond to each of the measured parameter. The use of standard file formats, such as an "FCS" file, for storing data from a flow cytometer facilitates analyzing data using separate programs and machines. Using current analysis methods, the data typically are displayed in 2-dimensional (2D) plots for ease of visualization, but other methods may be used to visualize multidimensional data.

The data obtained from an analysis of cells (or other particles) by multi-color flow cytometry are multidimensional; each cell corresponds to a point in a multidimensional space defined by the parameters measured. Populations of cells or particles are identified as clusters of points in the data space. The identification of the extent of a cluster and, thereby identifying the points in a population, can be carried out manually by drawing a gate (boundary) around a population displayed in one or more 2-dimensional plots of the data. Such plots are referred to as "scatter plots" or "dot plots". Alternatively, clusters can be identified, and gates that define the limits of the populations, can be determined automatically. A number of methods for automated gating have been described in the literature. See, for example, U.S. Pat. Nos. 4,845,653; 5,627,040; 5,739,000; 5,795,727; 5,962,238; 6,014,904; 6,944,338, each incorporated herein by reference.

The parameters measured using a flow cytometer typically include the excitation light that is scattered by the particle along a mostly forward direction, referred to as forward scatter (FSC), the excitation laser that is scattered by the particle in a mostly sideways direction, referred to as side scatter (SSC), and the light emitted from fluorescent molecules in one or more channels (range of frequencies) of the spectrum, referred to as FL1, FL2, etc., or by the fluorescent dye that is primarily detected in that channel. Different cell types can be identified by the scatter parameters and the fluorescence emissions resulting from labeling various cell proteins with dye-labeled antibodies.

Both flow and scanning cytometers are commercially available from, for example, BD Biosciences (San Jose, Calif.). Flow cytometry is described at length in the extensive literature in this field, including, for example, Landy et al. (eds.), Clinical Flow Cytometry, Annals of the New York Academy of Sciences Volume 677 (1993); Bauer et al. (eds), Clinical Flow Cytometry: Principles and Applications, Williams & Wilkins (1993); Ormerod (ed.), Flow Cytometry: A Practical Approach, Oxford Univ. Press (1997); Jaroszeski et al. (eds.), Flow Cytometry Protocols, Methods in Molecular Biology No. 91, Humana Press (1997); and Practical Shapiro, Flow Cytometry, 4th ed., Wiley-Liss (2003); all incorporated herein by reference. Fluorescence imaging microscopy is described in, for example, Pawley (ed), Handbook of Biological Confocal Microscopy, 2nd Edition, Plenum Press (1989), incorporated herein by reference.

BRIEF SUMMARY OF THE INVENTION

The present invention provides methods and systems for identifying clusters or populations in multidimensional data. The methods and systems are particularly applicable to identifying populations of cells or particles in multidimensional flow cytometry data.

For convenience, the methods of the present invention are herein referred to using the name "radial gating". The methods preferably are used for gating one or multiple cell populations presented as two-dimensional projections of multidimensional flow cytometry data, e.g., as represented in a typical 2-dimensional dot-plot. The methods preferably are used to create a polygonal boundary ("gate") around a cluster of data in 2-dimensional space. The methods can be extended to higher dimensions to, for example, create a polyhedronal boundary around a cluster of data in 3-dimensional space.

In one aspect, the present invention provides methods for identifying clusters or populations in multidimensional data that comprise the following steps:

1. segment the data space into a set of radial segments ("slices") originating at an originating point;
2. for each radial segment,
   a. generate a radial density histogram; and
   b. determine a cluster boundary from the radial density histogram; and
3. construct a gate surrounding the cluster from the cluster boundaries, each determined for a radial segment.

A gate surrounding the cluster constructed from a set of cluster boundaries, each determined for a radial segment, may have, in general, discontinuities at the radial segment boundaries (slice edges). In preferred embodiment, the final gate will be a continuous geometric object, wherein the cluster boundaries determined from the radial segments are constrained or modified such that the cluster boundaries for two adjacent radial segments are connected at the segment boundaries. More preferably, the gate will be defined in 2-dimensional space as a connected polygon surrounding the cluster, the polygon consisting of a connected set of linear boundaries.

Thus, the methods of the present invention preferably further comprise the step of constructing a continuous (connected) gate from the set of cluster boundaries, each determined for a radial segment. More preferably, the methods of the present invention further comprise the step of constructing a connected polygonal gate from the set of cluster boundaries, each determined for a radial segment.

In more preferred embodiments, the connected polygonal gate will be a convex polygon. The methods of the present invention further comprise the step of generating a convex polygonal gate from the initial polygonal gate.

Thus, the present invention further provides preferred methods for identifying clusters or populations in multidimensional data that comprise the following steps:

1. identify an originating point within the population to be identified;
2. segment the data space into a set of radial segments originating at the initial point;
3. for each radial segment,
   3a. generate a radial density histogram;
   3b. locate a cluster boundary from the radial density histogram;
4. construct a polygonal gate surrounding the cluster;
5. generate a convex polygonal gate.

In another aspect, the present invention provides an instrument capable of using the radial gating methods to identify clusters in multidimensional data. In a preferred embodiment, the instrument is a flow cytometer system that includes both the flow cytometer and a computer that carries out the data analysis.

The methods and systems of the present invention further enable automated batch processing of multiple data sets. In one embodiment, a template listing the location of the originating point, the number of radial segments, and the number of radial bins, is recorded and used for the analysis of subsequent data sets. The radial gate is then recomputed based on the data set being analyzed. Alternatively, the originating point is determined for each data set using any of a number of methods known in the art. Utilizing this overall process, the present invention can gate an entire database of similarly obtained data in an automatic manner without any user interaction other than the initial gates selected by the user on the first representative data set.

Some of the drawings may be simplified for clarity. Thus, the drawings may not depict all of the components of a given apparatus, device, system, method, or any other illustrated component or process Like reference numerals may be used to denote like features throughout the specification and figures.

DETAILED DESCRIPTION OF THE INVENTION

The following definitions are provided for clarity. Unless otherwise indicated, all terms are used as is common in the art. All reference cited herein, both supra and infra, are incorporated herein by reference.

As used herein, "system" and "instrument" and "apparatus" are intended to encompass both the hardware (e.g., mechanical and electronic) and associated software (e.g., computer programs) components.

In the methods of the present invention, a two-dimensional plane representing the data space is subdivided into a plurality of radial segments (slices), preferably equal-sized, each radiating from a single originating point. A "radial histogram", as used herein, refers to a one-dimensional histogram of particle counts in bins defined by distance from the originating point, within a single radial segment ("slice). A "radial density histogram", as used herein, refers to a one-dimensional histogram of particle count densities in the bins defined by distance from the originating point, within a single radial segment. The terms "radial histogram" and "radial density histogram" also are used to refer to two-dimensional histograms consisting of the set of one-dimensional histograms, indexed by the radial segment number, referred to as the "slice index". The dimensionality of the histogram will be clear from context. Bins of the histograms are indexed counting from the originating point.

As used herein, a "population" or "cluster" of particles, such as cells or synthetic particles, refers to a group of particles that possess optical properties with respect to one or more measured parameters such that measured parameter data form a cluster in the data space. Each measured parameter corresponds to one dimension of the data space. A cluster may be defined in a subset of the dimensions, i.e., with respect to a subset of the measured parameters.

As used herein, the term "polygon" refers to a closed plane figure bounded by straight lines. As used herein, the term "polyhedron" refers to a solid formed by plane faces.

The term "MFI", as used herein, refers to the mean or median fluorescence intensity of a population of fluorescence particles. It will be understood that other statistical measures of the population fluorescence, such as truncated mean or truncated median fluorescence, may be used.

The data obtained using a flow cytometer to analyze particles or cells may be transformed to facilitate analysis or display. For example, the data may be compressed using, for example, a log transform, although other transforms may be used. This optional data transformation facilitates visually recognizing population clusters within the data when displayed. The fluorescence intensity parameters typically are log-transformed or displayed on a log scale, whereas the scatter parameters typically are displayed on a linear scale. The methods of the present invention are exemplified herein using fluorescence MFI data that are transformed to a log scale with base 10. All MFI values less than 1 are converted to 1 before the log transformation to avoid obtaining negative transformed data. A linear scale is used for SSC parameter, all the events with SSC value less than 0, which result from noise in the detection system, are removed before gating. Parameters are then scaled to be in the range (0, 1000).

The data from the cell or particle populations preferably are compensated prior to the clustering analysis by the present methods. However, this is not a critical aspect of the invention, and the present methods can be used with uncompensated or partially compensated data. Compensation facilitates analysis of the data from multiply dyed particles by making the measurements of each of the dyes independent. Methods of compensation are known in the art and are described in, for example, Bagwell et al. "Fluorescence Spectral Overlap Compensation for any Number of Flow Cytometer Parameters", Ann. N.Y. Acad. Sci. 677, 167-184 (1993); Roederer et al., "Eight Color, 10-Parameter Flow Cytometry to Elucidate Complex Leukocyte Hetrogeneity", Cytometry 29, 328-339 (1997); and Bigos et al., Cytometry 36: 36-45 (1999), each incorporated herein by reference. WinList™ (Verity Software House, Topsham, Me.) is a stand-alone software package that allows software compensation on the stored data files produced by a flow cytometer. See also the whitepaper describing the BD FACSDiVa™ Option for the BD FACSVantage SE Flow cytometer (BD Biosciences, San Jose, Calif.; available at www.bdbiosciences.com), incorporated herein by reference.

DESCRIPTION BASED ON THE FIGURES

The figures depict aspects of the algorithmic aspects of the methods of the present invention as applied to an example data set. The methods are implemented as a computer program that takes a standard FCS data file as input. An FCS data file is a standard file for recording multidimensional flow cytometry data in tabular form, wherein each row corresponds to a particle, and each column corresponds to one of the measured parameters.

The FCS file was used to record data measured for four parameters consisting of one scatter parameter, SSC-A, and three fluorescence intensity parameters from three well-known fluorescence dyes, PE, PE-Cy7, and PE-Cy5 (more specifically PE-A, PE-Cy5-H, and PE-Cy7-A). The choice of parameters is for the convenience of the description and is not meant to limit the methods.

The three fluorescence parameters, PE-A, PE-Cy5-H, and PE-Cy7-A, were transformed to log scale with base 10. All values less than 1 were converted to 1 before log transformation. Linear scale was used for the SSC parameter, and all the events with SSC value less than 0 were removed before gating. Then all the four parameters are scaled to range (0, 1000).

In accordance with an embodiment of the present invention, the methods of the present invention comprise a cluster-finder algorithm that can be used with event data such as dot plots or scatter plots of data obtained via flow cytometry. The cluster-finder algorithm of the present invention preferably comprises the following steps:
1. identify an initial point, also referred to as an originating point, within the population to be identified;
2. segment the data space into a set of radial segments originating at the initial point;
3. For each radial segment,
    a. generate a radial density histogram;
    b. locate a cluster boundary from the radial density histogram;
4. construct a polygonal gate surrounding the cluster;
5. generate a convex polygonal gate.

Figure 1:
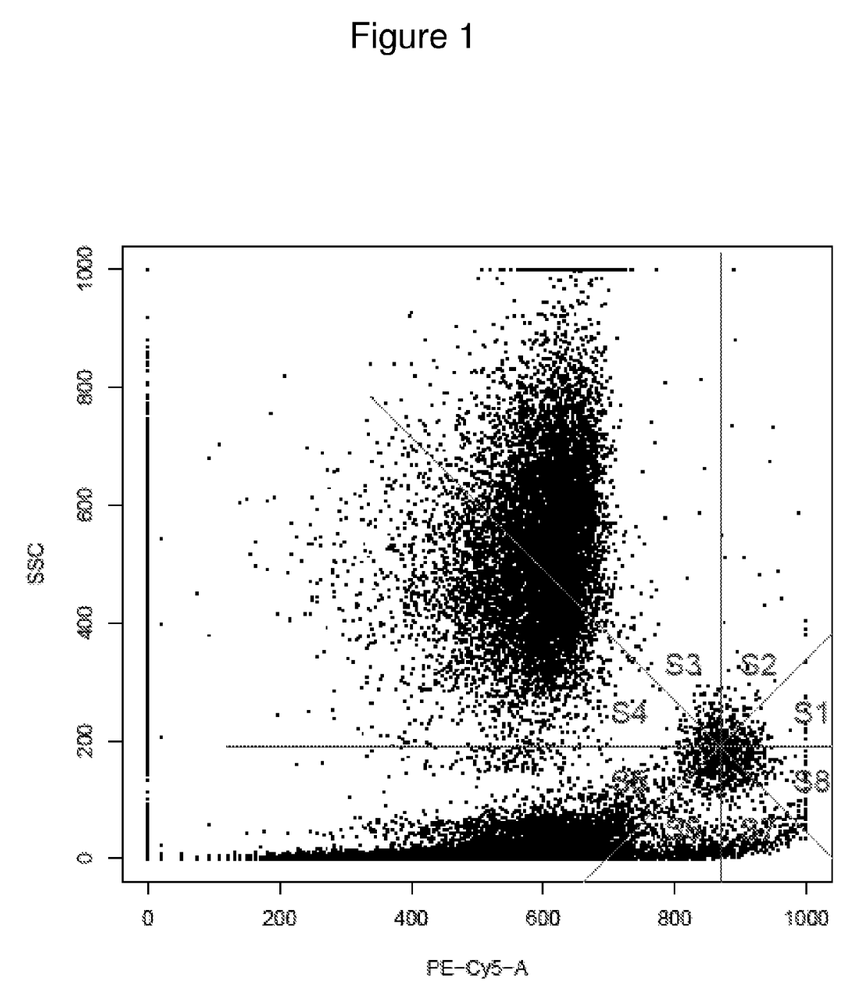
FIG. 1 illustrates method of a determining a population using radial density histograms.

FIG. 1 shows an exemplary dot-plot (scatter plot) of SCC versus PE-Cy5 fluorescence. The exemplary data provided in FIG. 1 will be processed in accordance with the present invention and described below in connection with FIGS. 1-5 for illustrative purposes. More detailed descriptions of the steps are provided in the examples.

1. Identify an Originating Point

The initial or originating point is a point that within the population to be identified. The exact location is not critical to the methods. However, it is helpful to select a point that is approximately close to the center of the cluster, or the region of highest density.

A number of methods can be used to select the initial point. In manual-assisted gating, the selection of the initial point is carried out visually by an operator. Alternatively, any of the known algorithms to identify the approximate center of a cluster can be used.

As shown in FIG. 1, the population of interest is the globular population in the lower right side of the plot. The originating point chosen is the intersection of the radial lines.

2. Segment the Data Space into a Set of Radial Segments

As shown in FIG. 1, the data space is divided into eight radial segments (slices) defined by lines segments originating at the originating point and radiating out. The radial segments are labeled S1 through S8.

The number of radial segments will determine the maximum number of sides of a final polygonal gate. To create a two dimensional polygonal gate, the data space is divided into a minimum of three radial segments. In general, a higher number radial segments is desirable, depending on the complexity of the population boundaries and the accuracy of the fit desired. For the analysis of cell populations by flow cytometry, the 2-dimensional data space is subdivided by from about 8 to about 16 radial segments.

Preferably, all the angles formed by two adjacent lines are the same. However, this is not critical, and in some embodiments, it may be desirable to divided some regions of the 2-dimensional data space into more radial segments than others in order to allow for more accurate gating in particular directions.

3a. Generating a Radial Density Histogram

Figure 2:
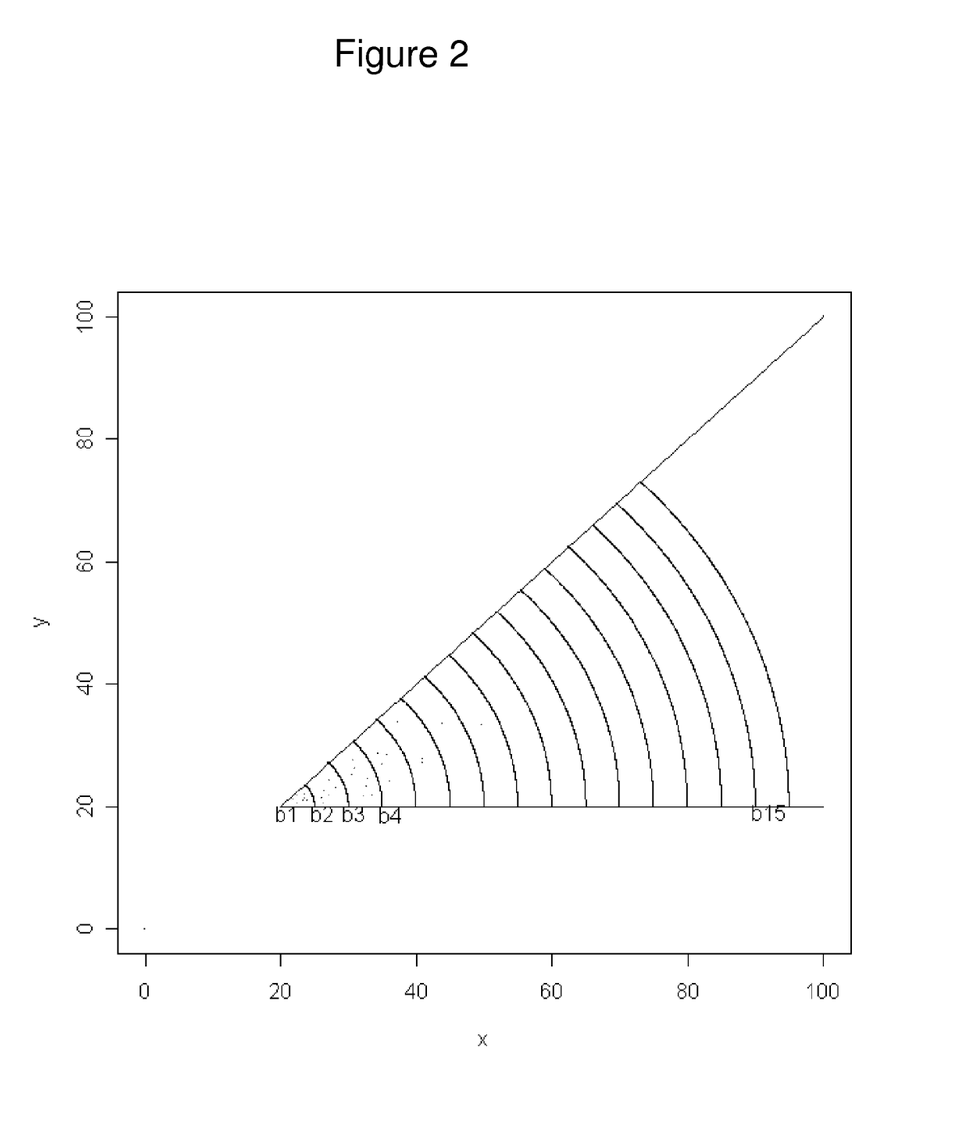
FIG. 2 further illustrates a method of a determining population using radial density histograms.

FIG. 2 depicts the subdivision of one of the radial segments, radial segment S1 (labeled in FIG. 1), into a series of radial-bins defined by a lower and an upper distance from the originating point. The distance between the lower and upper distances is the width of the radial-bin ("radial bin width"). Preferably, the width of each radial-bin will be the same. For example, as shown in FIG. 2, radial-bin b1 corresponds to a region within the radial segment having a distance from the originating point of less than 1 radial-bin-width; radial-bin 2 corresponds to a region within the radial segment having a distance from the originating point of between 1 radial-bin-width and 2 radial-bin-widths, etc.

A radial histogram is calculated as a histogram having bin-widths corresponding to the radial-bin-widths. The value of the histogram indexed by the bins is corresponds to the number of data points observed within the corresponding radial-bin. In the example of FIG. 2, the radial segment is divided into 15 bins, As illustrated in FIG. 2, radial segment S1 is divided into 15 bins, b1, b2, b3, . . . , b15, each of bin width 5. The radial histogram, $h1, =(7, 6, 7, 4, 3, 1, 1, 0, \ldots, 0)$, which means 7 points in bin b1, 6 events in bin b2, and so on. It should be noted that, because the area of a radial-bin increases with distance from the originating point, the radial histogram records the total number of data points observed within each radial-bin, but does not reflect the density with the radial-bin.

Figure 3:
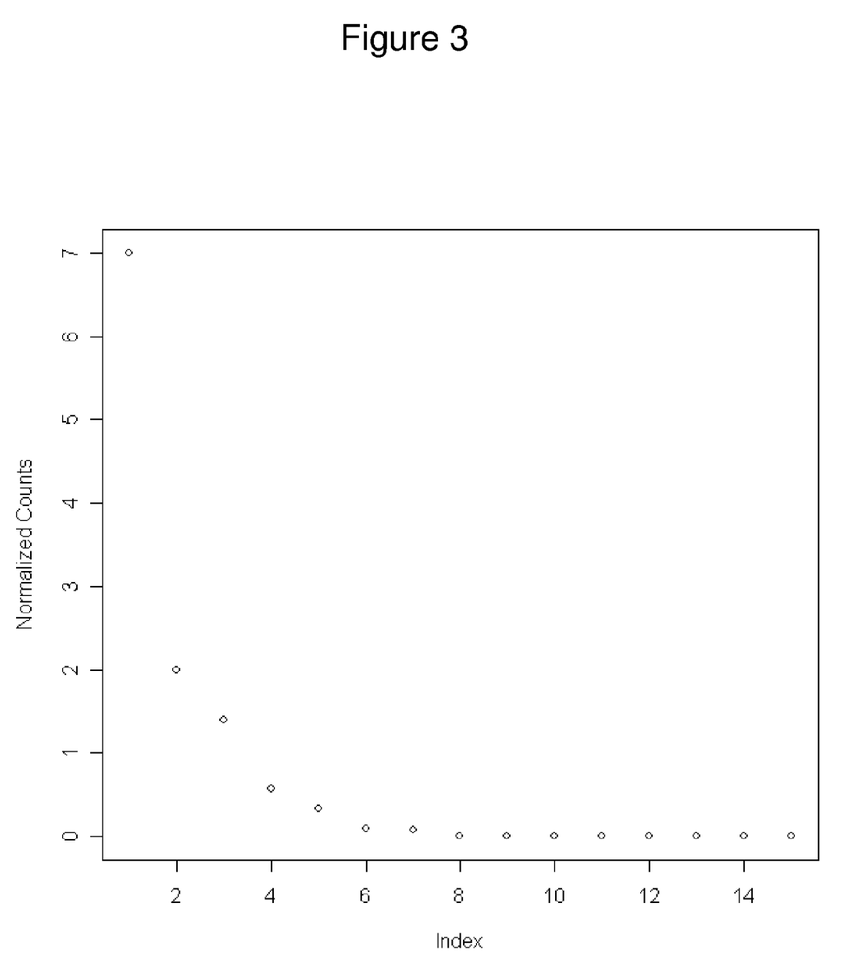
FIG. 3 further illustrates a method of a determining population using radial density histograms.
Figure 4A:
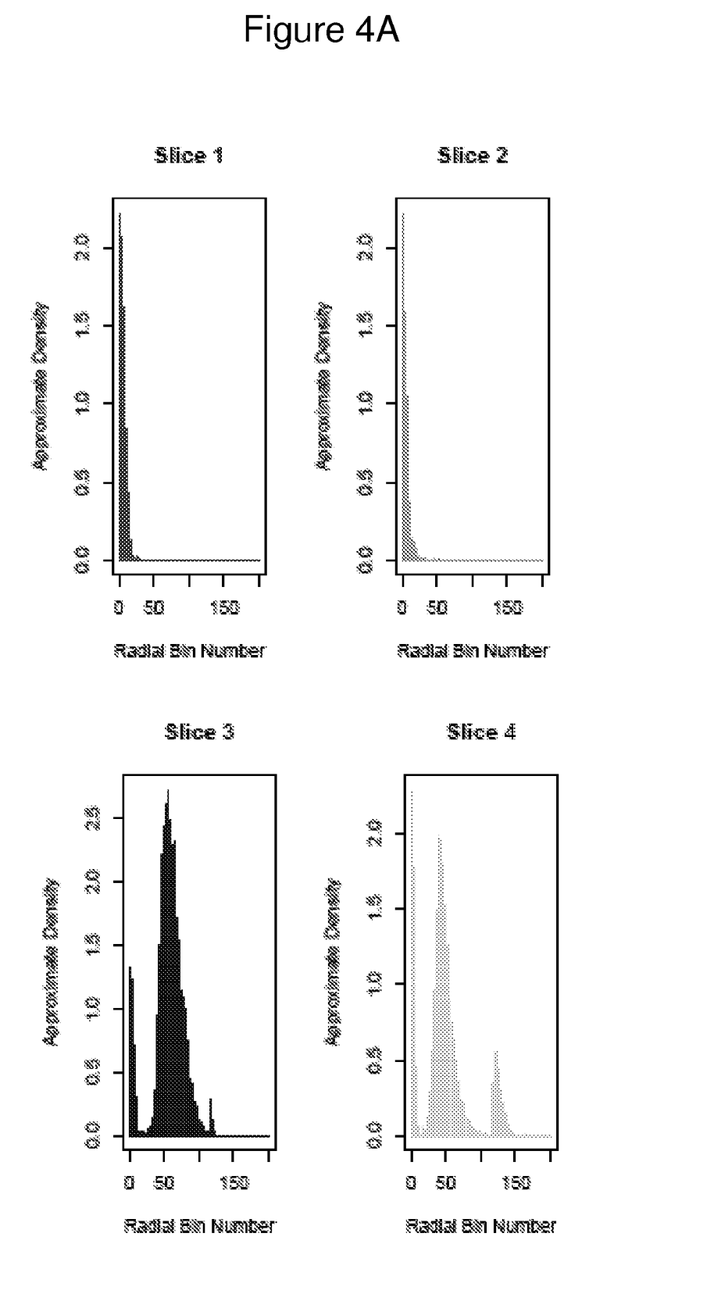
FIGS. 4A and 4B further illustrate a method of a determining population using radial density histograms.
Figure 4B:
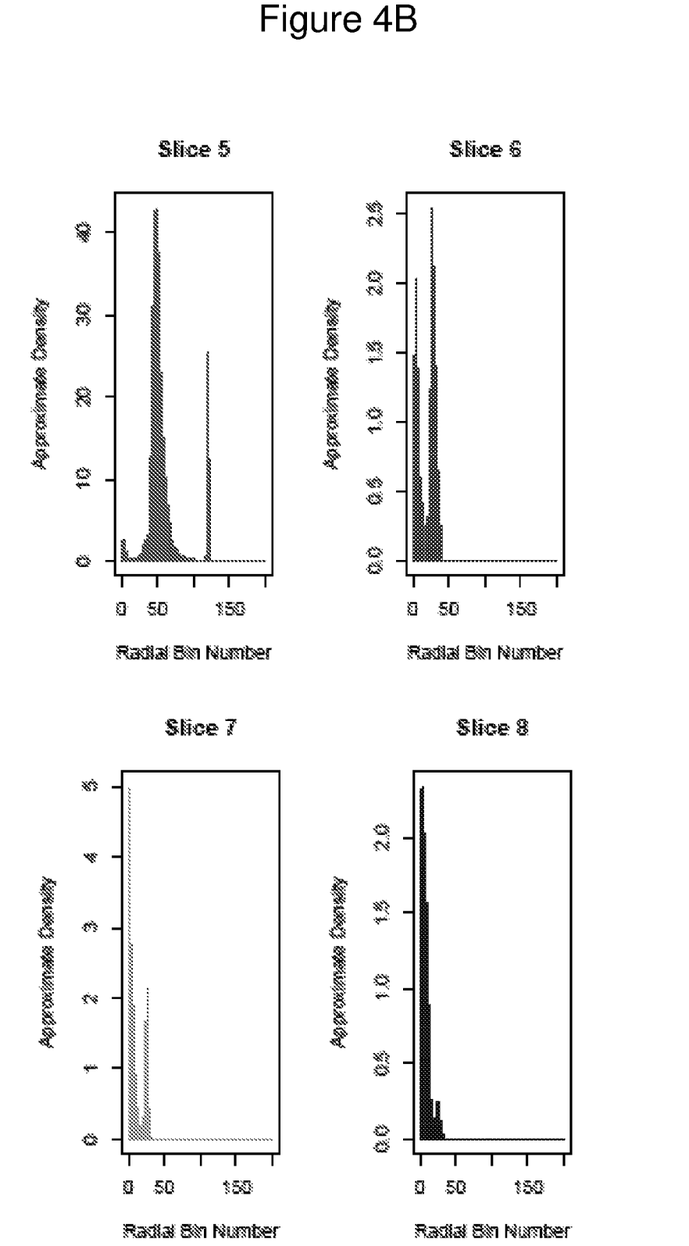

A radial density histogram is calculated from the radial histogram by normalizing the value in each bin by the area of the radial-bin. Thus, the radial density histogram provides a measure of the density within each radial-bin, ordered with increasing distance from the originating point. The radial density histogram for radial segment S1 is shown in FIG. 3. The radial density histogram, $h2, =(7, 2, 1.4, 0.57, 0.33, 0.09, 0.07, 0, \ldots, 0)$. The density values are calculated assuming the area of bin b1 is one area unit. The radial density histograms for each of the slices are shown in FIGS. 4A and 4B.

Optionally, the radial density histogram of normalized bin values may be smoothed by, for example, a moving-averaging smoothing method, or other smoothing technique well known in the art. Smoothing decreases the effect of random fluctuations in the particle density and may facilitate obtaining a more accurate population gate.

3b. Locate the Cluster Boundary from the Radial Density Histogram

A boundary of a cluster along a radial segment is identified from the radial density histogram for that segment. A boundary is calculated using one of two methods, either threshold method or a valley method, or a combination of the two. The threshold method is appropriate if the density of the histogram decreases monotonically with distance away from the originating point. For example, by inspection of the population of interest in FIG. 1, the density in radial segment S1 decreases with increasing distance from the originating point. In this case, the limit of the population is the distance beyond which the density of the population falls below a given threshold. The valley method is appropriate if the density of the histogram is bimodal due to the presence of a second population. In this caser, the boundary is set at a local density minimum (valley) separating the two populations. However, if the density between the populations first falls below a threshold, then the boundary is set using the threshold method despite there being a second population farther away. For example, in radial segment S4, the density decreases with increasing distance from the originating point, but then increases farther away. The density minimum between the populations is essentially zero, and the threshold method is likely to be appropriate.

The two methods can also be used in combination to determine the true boundary for each slice. For example, the first method may be used for some of the slices and the second method may be used for other slices. In another embodiment the boundary for a particular slice may be estimated according to both methods and the boundary may be determined as a function of the two estimates. For example, the boundary may be the maximum, minimum, average, or other function of the two estimates.

The set of boundaries determined for each radial segment ("slice") define a boundary for the population that encompasses the population. A boundary defined as a distance from the originating point within a slice is an arc segment extending from one edge of the slice to the other edge of the slice. As the distances of the boundaries from the originating point will typically be different between slices, the set of boundaries forms a radial gate consisting of a set of arc segments, with the discontinuities present at the slice edges.

Preferably, the cluster boundaries within each radial segment will be line segments, rather than arc segments. The radial segment cluster boundary can be determined initially as a radial distance from the originating point, and then a line segment cluster boundary can be defined based on the radial distance (arc segment) cluster boundary. The use of a line segment to define the cluster boundary is an approximation of the arc segment cluster boundary. For example, a line segment connecting the intersection points of the arc segment and the sides of the slice may be used to define the cluster boundary in the slice. This cluster boundary will enclose a somewhat smaller area than that enclosed by an arc segment, as the distance from the originating point to the line segment in the interior of the radial segment will be less than the distance to the corresponding arc segment. Alternatively, a line segment that is tangential to the arc segment at the midpoint of the arc segment may be used to define the cluster boundary in the radial segment, and will enclose a slightly larger area that enclosed by the arc segment. Alternatively, a line segment boundary may be selected that will preserve the total area of the region enclosed. Gates defined as the collection of line segment cluster boundaries, each corresponding to a radial segment, can have discontinuities at the radial segment boundaries.

Figure 5A:
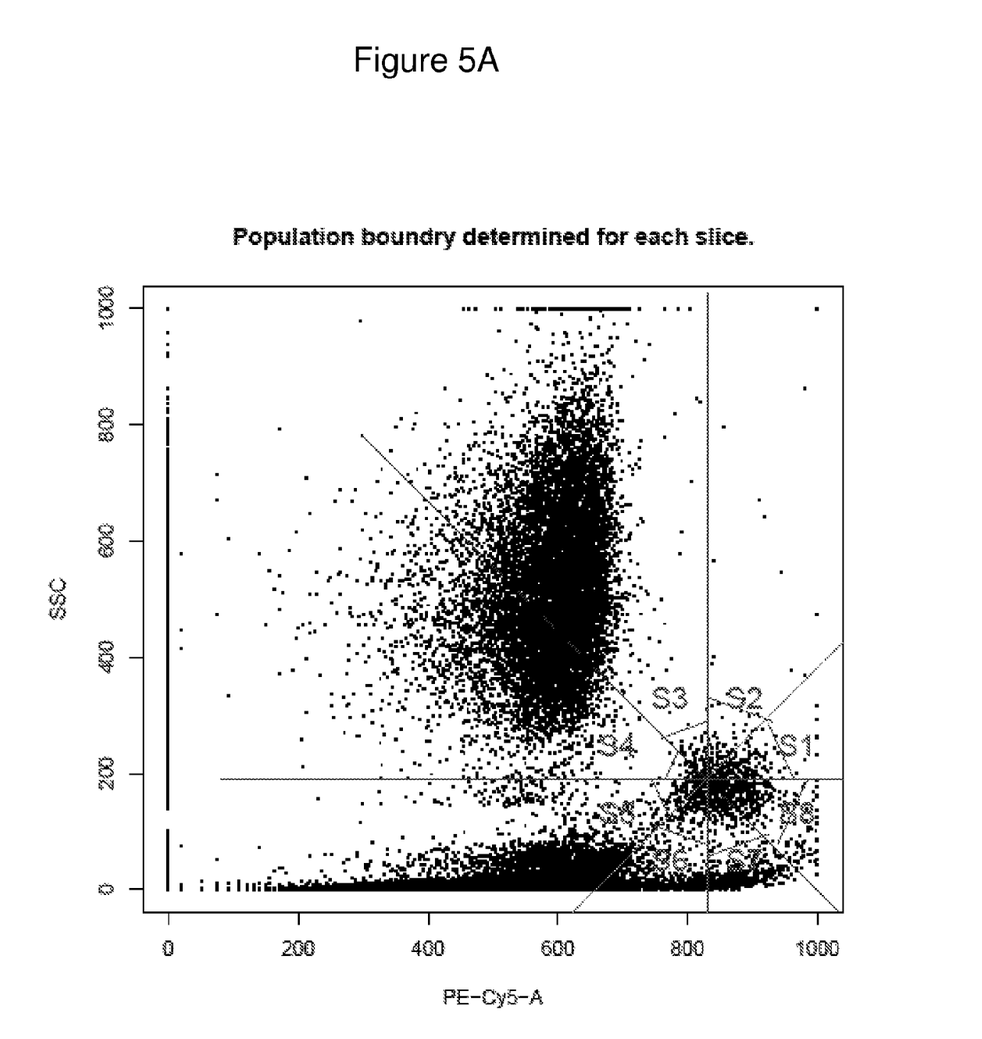
FIGS. 5A-5C further illustrate a method of a determining population using radial density histograms.

The population gate defined as a set of line segments is shown in FIG. 5A.

4. Construct a Polygonal Gate Surrounding the Cluster

In preferred embodiments, the gate is a continuous (connected) geometric object, wherein the cluster boundaries determined from the radial segments are constrained or modified such that the cluster boundaries for two adjacent radial segments are connected at the segment boundaries. More preferably, the gate will be defined in 2-dimensional space as a polygonal surrounding the cluster, the polygon consisting of a connected set of linear boundaries.

A connected polygon can be derived from a radial boundary defined as a set of line segments by modifying one or both of the intersection points of the segments with the shared slice boundary such that the two segments are connected. This can be carried out by choosing the farther or closer of the two intersection points, or by choosing a third point located between the two points. The selection of the point is not a critical aspect of the invention.

Figure 5B:
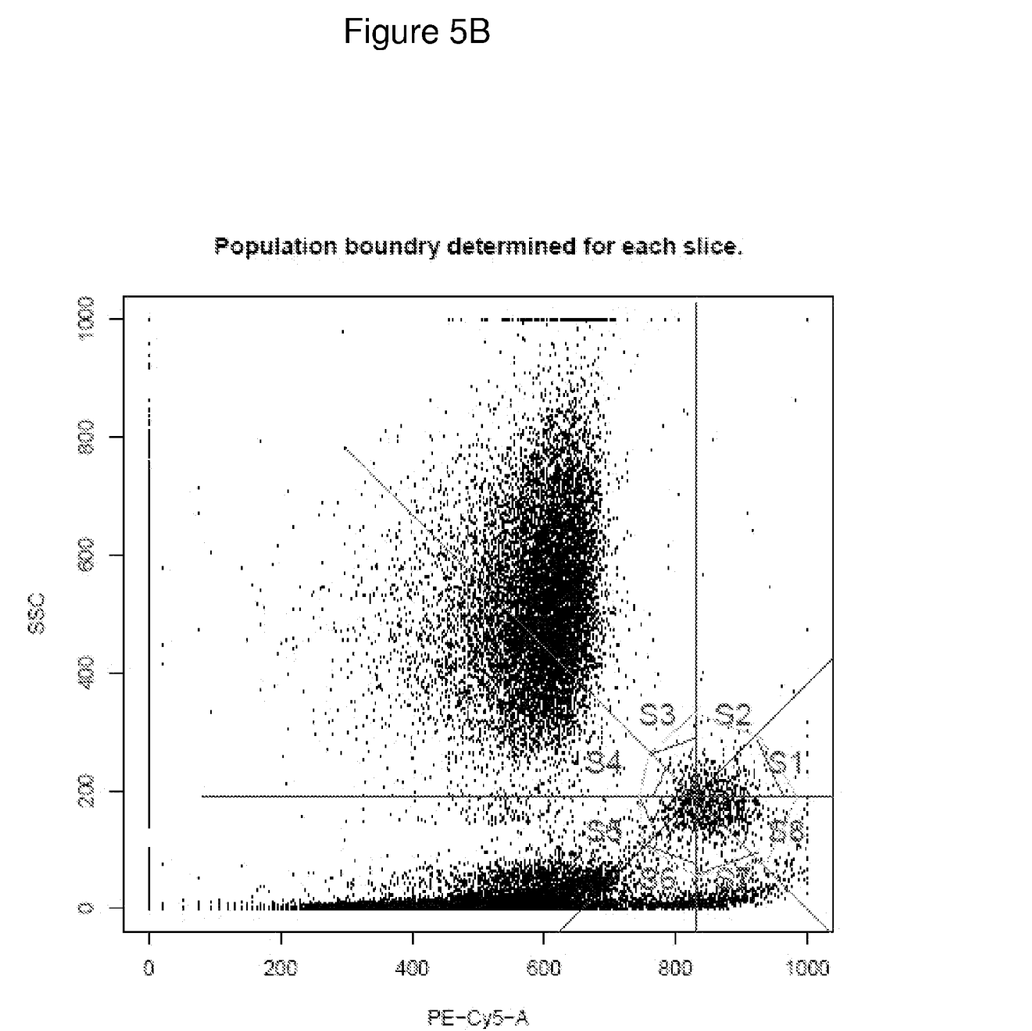

The population gate defined as a set of connected line segments is shown in FIG. 5B. In this example, the farther of the two intersection points along a slice edge was chosen as the polygon vertex.

5. Generate a Convex Polygonal Gate

Figure 5C:
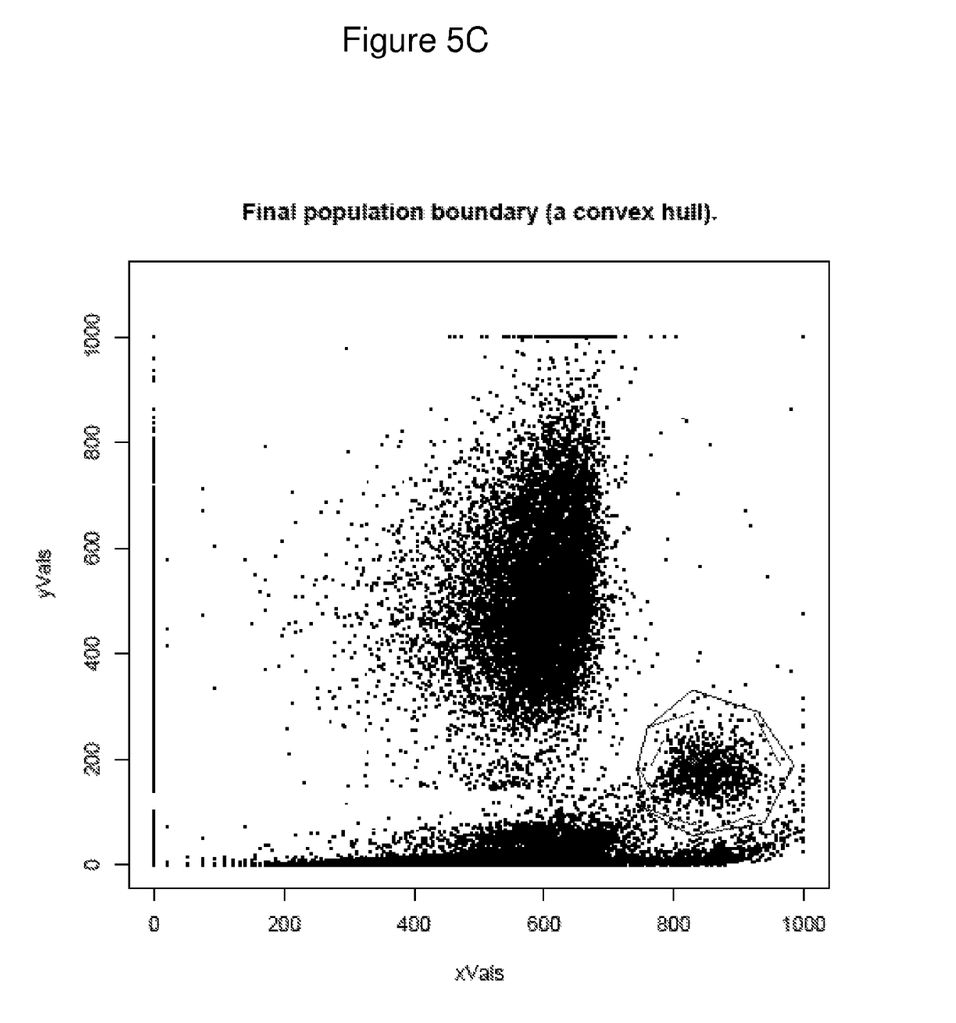

In preferred embodiments, the polygon gate is converted to a convex polygon, if it is not already a convex polygon. The final gate shown in FIG. 5C is a convex polygon and does not need to be altered. In general, a polygon, defined by a set of points, can be converted to a convex polygon by removing any vertex that is not convex, which is any vertex that has an interior angle of greater than pi.

Figure 6:
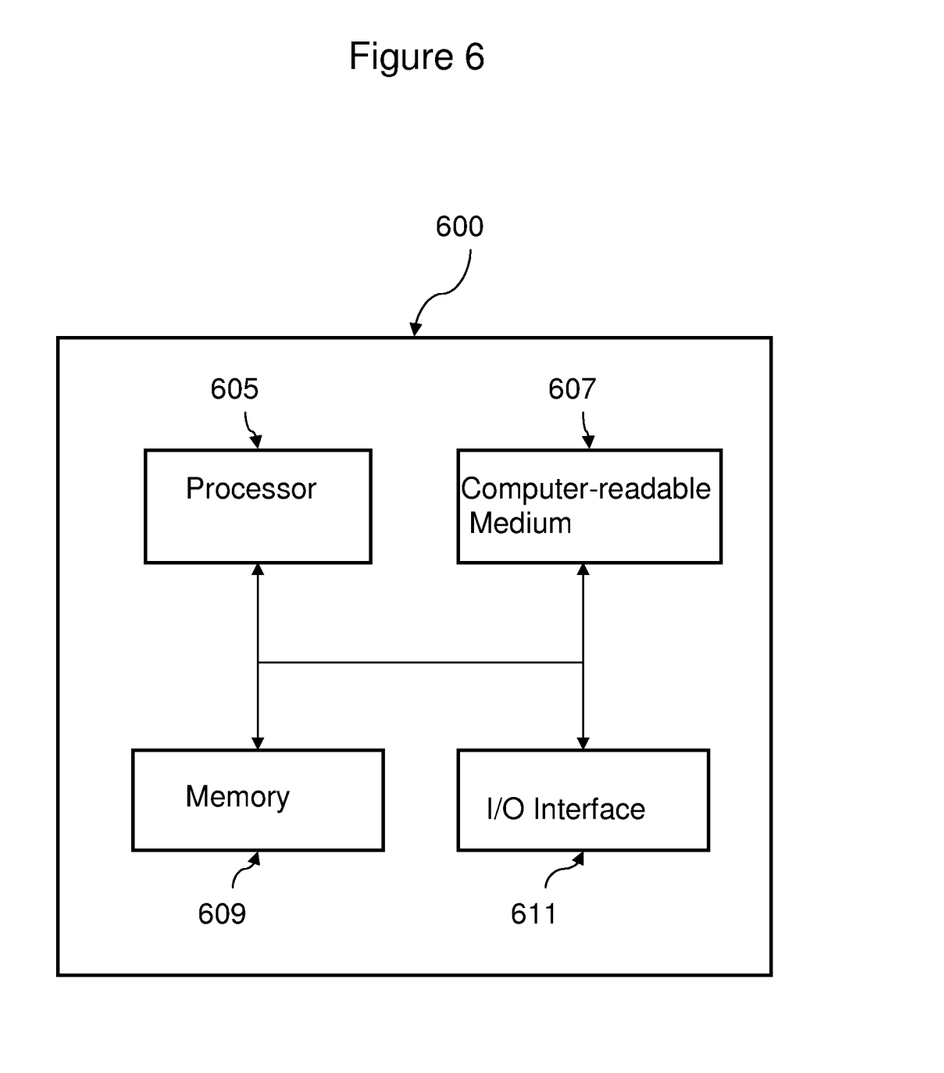
FIG. 6 illustrates an apparatus for implementing the methods described herein.

FIG. 6 illustrates an apparatus 600 configured to perform the methods described herein. The apparatus 600 comprises a processor 605 connected to a computer-readable medium 607, a memory 609, and an input/output interface 611. The apparatus 600 may perform the functionality described above. In particular, the processor 605 may configure to perform the steps of the methods described herein. The computer 607, may comprise instructions which, when executed, cause the processor 605 to perform the functionality described herein. The memory 609 may be configured to store the variables and other data described herein. The I/O interface 611 may be configured to receive communications from external devices or users and to communicate information to external devices or users.

Those skilled in the art will recognize how best to implement the described functionality presented throughout this disclosure depending on the particular application and the overall design constraints imposed on the overall system. The description is provided to enable any person skilled in the art to fully understand the full scope of the disclosure. Modifications to the various configurations disclosed herein will be readily apparent to those skilled in the art.

EXAMPLES

The examples describe the algorithmic aspects of the methods of the present invention. While this invention is satisfied by embodiments in many different forms, the embodiments shown in the drawings and described herein in detail are preferred embodiments of the invention, with the understanding that the present disclosure is to be considered as exemplary of the principles of the invention and is not intended to limit the invention to the embodiments illustrated.

It should be noted that some variables defined for use within a step of the method may be named using the same variable names as used to identify a different variable in a different section. The naming of variables within an algorithm is arbitrary, and variables defined within one section are not to be confused with variables defined in other sections that are designated with the same name.

Example 1

Construction of a Radial Density Histogram

A "radial segment", also referred to as a "slice", refers to a region of the data space formed by dividing the space by a plurality of line segments radiating from the origination point, as defined above. The originating point is designated O=(ox, oy).

A "slice index" or "radial segment index" refers to a designation of the slices according to an indexing scheme. Typically, the slices are indexed by counting the slices clock-wise or counter-clockwise, starting with an initial slice.

"NumSlice" is the total number of slices. The number of slices is chosen prior to the subdividing the data space, as described above.

"bin width" refers to the width of a bin in a histogram measured as a distance from the originating point. The bin width within a slice is assumed be constant, but may differ between slices. The bin widths are designated R=($R_1$, $R_2$, . . . , $R_{NumSlice}$), respectively.

For any given point A=(x, y) in the data space, the following steps are used to calculate the point A's slice index and bin index.

Calculate the Slice Index

The slice index of point A, which identifies the slice that point A lies in, is calculated as follows:
1. Calculate slice angle to be 2*pi/NumSlice, and denote it as sliceWid. Then the first slice has angle from 0 to sliceWid originating from point O, and second slice has angle from sliceWid to 2*sliceWid, and so on.
2. Get tangent value of point A to point O by formula (y−oy)/(x−ox), and denote it as tanVal.
3. If y>=oy, then A is in slice with angle in [0, pi).
   3.1. If x>ox, slice index is calculated by the formula floor(a tan(tan Val)/sliceWid)+1, where floor(r) is the largest integer no greater than r, and a tan(r) is the arc-tangent value of r.
   3.2. Else if x=ox, the slice index is NumSlice/4+1.
   3.3. Else if y>oy, slice index is calculated by formula:

NumSlice/2−ceiling(a tan(−tan Val)/SliceWid)+1, where ceiling(r) take the smallest integer no smaller than r.
   3.4. Else slice index is NumSlice/2+1.
4. Otherwise, A is in slice with angle in [pi, 2*pi).
   4.1. If x<ox, slice index is calculated by the formula:

NumSlice/2+floor(a tan(tan Val)/sliceWid)+1.

4.2. Else if x=ox, slice index is NumSlice/4*3+1.
   4.3. Else slice index is calculated by formula:

NumSlice−ceiling(a tan(−tan Val)/SliceWid)+1.

5. Denote the slice index to be sInd.

Calculate the Bin Index

The bin index of point A in slice sInd is determined by the bin width $R_{sInd}$, and is calculated by the formula:

ceiling($\sqrt{(y-oy)^2+(x-ox)^2}/R_{sInd}$).

Construct a Radial Histogram

The slice index and bin index are determined for each point in the data. The number of data point having each slice index and bin index are recorded in a 2D radial histogram sHist[s,b], wherein sHist[s,b] denotes the number of points in bin b of slice s.

Normalize the Radial Histogram to Obtain a Radial Density Histogram

The 2D radial histogram sHist[s,b] is normalized by relative bin area to obtain a radial density histogram. In the case that the bin width is constant for all slices, the radial histogram, sHist[s,b], is normalized by dividing the count in bin b by 2*b−1, where b is the number of the bin counting outward from the originating point. This is used to normalize the bin count within a slice, and does not normalize the bin count across slices when different bin widths are applied in different slices.

In the case that different widths are used in different slices, then the radial histogram sHist[s,b] is normalized by dividing the count in bin b by (2*b−1)*r[s]*r[s]/2, where r[s] denotes the bin width used for slice s. This is used to normalize the bin count across slices when different bin widths, r, are applied in different slices.

Calculate the Intersections Between a Bin Boundary and the Slice Edges

The intersections of a bin boundary with the slice edges are obtained for use in defining a preliminary gate boundary, as described in the example 2, below. Given bin index bIdx and slice index sIdx, the two points corresponding to the intersections of slice edges and the bin edge are obtained as follows.
1. If slice sIdx is on the top half of the plane originating at (ox, oy), i.e. 1<=sIdx<=NumSlice/2,
   1.1. alpha=(sIdx−1)*2*pi/NumSlice
   1.2. beta=sIdx*2*pi/NumSlice
   1.3. $dx_1$=bIdx*$R_{sInd}$*cos(alpha)
   1.4. $dy_1$=bIdx*$R_{sInd}$*sin(alpha)
   1.5. $dx_2$=bIdx*$R_{sInd}$*cos(beta)
   1.6. $dy_2$=bIdx*$R_{sInd}$*sin(beta)
   1.7. The first intersection has coordinates ($x_1$, $y_1$), wherein $x_1$=$dx_1$+ox, and $y_1$=$dy_1$+oy
   1.8. The second intersection has coordinates ($x_2$, $y_2$), wherein $x_2$=$dx_2$+ox, and $y_2$=$dy_2$+oy
2. If slice sIdx is on the bottom half of the plane originating at (ox, oy), i.e. NumSlice/2<sIdx<=NumSlice
   2.1. alpha=(sIdx−NumSlice/2−1)*2*pi/NumSlice
   2.2. beta=(isIdx−NumSlice/2)*2*pi/NumSlice
   2.3. $dx_1$=bIdx*$R_{sInd}$*cos(alpha)
   2.4. $dy_1$=bIdx*$R_{sInd}$*sin(alpha)
   2.5. $dx_2$=bIdx*$R_{sInd}$*cos(beta)
   2.6. $dy_2$=bIdx*$R_{sInd}$*sin(beta)
   2.7. The first intersection has coordinates ($x_1$, $y_1$), wherein $x_1$=−$dx_1$+ox, and $y_1$=−$dy_1$+oy
   2.8. The second intersection has coordinates ($x_2$, $y_2$), and $x_2$=−$dx_2$+ox, and $y_2$=−$dy_2$+oy

Example 2

Determination of Radial Density Histogram Boundaries

The 2D radial density histogram calculated in example 1, above, is used to determine the boundaries of a population in the two dimensions. A boundary is calculated for each 1D radial density histogram. Two methods are used to determine the boundary for each slice: a (1) threshold method and a (2) valley method. The threshold method is appropriate if the density of the histogram decreases monotonically with distance away from the originating point. In this case, the limit of the population is the distance beyond which the density of the population falls below a given threshold. The valley method is appropriate if the density of the histogram initially decreases with distance away from the originating point, but then subsequently increases, is bimodal. A bimodal histogram indicates that there is a second, separate population, and a boundary between the two populations is identified by the valley in the density between the two populations. The two methods can also be used in combination to determine the true boundary for each slice. The two methods of determining a boundary within a given slice density histogram, sHist[s,b], (i.e., for a given slice s of the 2D radial density histogram), are described more fully, below.

Threshold Method of Finding a Boundary

The threshold method finds the boundary by locating the first bin in the slice having less than a threshold density, preferably measured as a percentage (f_thr %) of the peak bin count, and defining this first bin as the boundary bin. Identification of a peak within a slice density histogram is carried out because the origination point may not have been positioned at the maximum population density. Thus, in any given slice, the density initially may increase with distance away from the origination point, corresponding to moving closer to the true population maximum density, and then decrease.

The following steps are used to find the boundary bin, which has less than f_thr % count of peak bin.
1. Find the first peak bin in the slice histogram. Starting from the first bin in the slice histogram, find the first bin which has more counts than the next adjacent bin. This bin is considered as the first real peak bin, and the bin index or the peak bin is denoted as j.
2. The threshold is set to be (f_thr %)*sHist[s,j], and is denoted as thr.
3. Starting from bin j, find the first bin with a count less than thr. This bin is denoted as the boundary bin.

Valley Method of Finding a Boundary

The valley method finds the boundary by locating the first valley bin in the slice. A bin is defined as a valley when the bin has count less than the counts of a given number (r), of adjacent bins. To ensure that a valley is a true valley and not due to a localized spike in the density, a percentage (f_v %), is employed to check if the valley bin has less than f percentage peak bin counts.
1. Find the first peak bin in the slice histogram. Starting from the first bin in the slice histogram, and find the first bin which has more counts than the next adjacent bin. This bin is considered as the first real peak bin, and the bin index is denoted as j
2. The threshold is set to be (f_v %)*sHist[s,j], and is denoted as val_thr
3. Starting from bin j, find the first bin with counts less than val_thr, and with count less than the counts of its r adjacent bins from either direction. This bin is denoted as the boundary bin.

The set of slice boundaries determined for each slice, as described above, define a boundary for the population. The boundary of a slice bin identified as a boundary bin is an arc segment extending from one edge of the slice to the other edge of the slice. The intersections of the bin boundary with the slice edges are as calculated above. As the distances of the slice bins from the originating point will typically be different between slices, the set of slice boundaries forms a radial gate consisting of a set of arc segments, with the discontinuities present at the slice edges.

Example 3

Calculation of a Connected Gate

The discontinuous radial gate determined using the methods described in example 2, above, provides the boundaries of the population. However, it is preferable to modify the initial gate to create a connected polygon, i.e., to identify a connected polygon that encloses the population. This section describes how to obtain a connected polygon gate for a population by using a radial density histogram and the boundary determination thresholds obtained using the methods of example 2, above.

The following variables are defined and used in the methods described in this example to construct a connected polygon gate. It should be noted that some of the variable names are used to identify different variables in the other sections. The variables defined herein are used within this section, and are not to be confused with variables in other sections that are designated with the same name.

The originating point O=(ox, oy) for the 2D radial density histogram

The number of slice $2^s$ for 2D radial density histogram, and s is an integer no less than 2. The number of slices is determined by the shape and the boundary complexity of the population to be gated, the latter is more important in determining the number of slices. The boundary complexity of a population is determined by the population's separation from other populations or debris. The poorer the separation, the more complex the boundary needs to be to separate the populations.

A vector r of length $2^s$ to define the bin width for each slice for 2D radial density histogram A vector f of length $2^s$ to define the percentage threshold used in each slice histogram to find the threshold boundary for the slice A vector t of length $2^s$ to define the percentage threshold used in each slice histogram to find the valley boundary for the slice A vector edgeBoundary of length $2^s$ to record the edge boundaries for the slice A Boolean vector checkMin of length $2^s$ to define if a valley threshold calculation is needed to determine the boundary for the slice A Boolean variable, rmSpike, to decide if a calculated boundary will be replaced by its neighbor median if the boundary is a spike. This is an optional, but provides improved results in some applications. If it not to be used, the value can be set to false.

A vector of points, designated pts, to store the list of points that defines the connected gate.

The following steps are used to calculate a connected gate. Initially, the following parameter values are set: getGateFlag=FALSE and getGateErrorCode=0.
1. Construct a 2D radial density histogram for the given events with values on two parameters.
2. Optionally, replace the first bin density value in each slice by the average of all the first bin density values in all slices. If the average first bin density value is no more than 0, set getGateFlag=TRUE, and getGateErrorCode=1. A non-positive average first bin density value indicates that the originating point was not actually placed inside a population and should be reposition. This step enables the algorithm to be stopped at this point (i.e., a "return" instruction) to allow for corrective action.

3. For each slice histogram, find the boundary bin index using the following steps:
   3.1. Smooth the slice histogram. Smoothing methods suitable applicable to histograms are well known in the art. The degree of smoothing is not a critical aspect of the invention.
   3.2. Define the maximum number of bins, maxBin, used to find non-zero bin count as the smallest integer no smaller than the value of 21 divided by bin width r for the slice. If the counts for the first maxBin bins are all zero, set the boundary bin index for the slice to be 0 and move to the next slice.
   3.3. Find the boundary bin index by using the threshold method with threshold f for the slice, and denote it as boundaryBin.
   3.4. If the checkMin value is true for the slice, then find a new boundary bin index by the valley method with threshold t for the slice. Check if the new boundary bin index is smaller than boundaryBin, and assign the new boundary bin index to boundaryBin if the new one is smaller.
   3.5. boundaryBin is the boundary bin index for the slice.
4. If rmSpike is true, use the following steps to remove spikes with a given factor fac, and obtain a new boundary set.
   4.1. For each boundary bin starting from slice one to $2^s$, calculate the median and robust SD of the 5 boundary distances including the boundary bin and its four closest neighbor bins (two from each side). Denote then mean and robust SD as m and Rsd.
   4.2. If Rsd is zero, replace Rsd by the standard deviation of the five boundary distances multiplying 2/fac.
   4.3. If the boundary distance of bin i is more than fac times Rsd different from the m, the boundary is identified as a spike boundary. The boundary index of the bin is replaced by m/r[i].
   4.4. If any spike is found in step 4.1 to 4.3, repeat the steps 4.1 to 4.3 until no spike boundary is found.
5. For each boundary bin index in a slice, compare it with the boundary bin index of its previous slice (defined as anti-clock order) by considering their bin width as well. For boundary bin index i,
   5.1. If boundaryBin[i]*r[i] is less than boundaryBin[i−1]*r[i−1], calculate edgeBoundary[i] to be boundaryBin[i−1]*r[i−1]/r[i]; otherwise, edgeBoundary[i] is set to be boundaryBin[i].
6. Convert each edgeBoundary value to corresponding point on the first edge of the slice, which is the intersection between the bin boundary and the slice edge obtained as described in example 1. Denote the points in pts, where pts[i,] denote the (x,y) coordinates of $i^{th}$ point.
7. Check if any obtained points having y value below zero and replace any point with a negative y value by one or two points with y value equal to zero. For each point starting from 1 to $2^s$
   7.1. If the y value is no less than zero, keep the point.
   7.2. Otherwise, set curr=i, prev=i−1 or $2^s$ if i=1, and foll=i+1 or 1 if i=$2^s$,
       7.2.1. If pts[prev, 2]>0, replace the point by a new point which is the intersection of the edge from pts[pre,] to pts[curr] and line y=0.
       7.2.2. If pts[foll, 2]>0, replace the point by (or add) a new point which is the intersection of the edge from pts[curr,] to pts[foll,] and line y=0.
8. Denote the updated point list as pts again, and there might more than, less than, or exactly $2^s$ points.
9. Return the points pts, getGateFlag, and getGateErrorCode.

Example 4

Converting a Polygon to a Convex Polygon

In preferred embodiments, the polygon gate is converted to a convex polygon, if it is not already a convex polygon. The following algorithm converts a polygon, defined by a set of points, to a convex polygon by removing vertices. The procedure is repeated multiple times till a convex polygon obtained.

An n-vertex polygon is denoted as a set of points, Pts={$(x_i, y_i)$}, where i=1, . . . , n. All the points are checked in anti-clock-wise order to see if any point is not a convex point. If such a point is found, it is removed from the vertices list.
Calculate Angle for a Segment with Direction
For a segment starting from point $(x_2, y_2)$ to $(x_1, y_1)$, the following calculations are used to calculate the angle of the segment.
1. Calculate $x=x_2-x_1$ and $y=y_2-y_1$
2. Calculate $\cos Val = X/\sqrt{x^2+y^2}$
3. If y is no less than 0, then the angle is a cos(cos Val); otherwise the angle is pi+a cos(−cos Val), where a cos (cos Val) calculate the arc-cosine value of cos Val
Check if a Vertex is a Convex Vertex
For a given point $(x_i, y_i)$, the two edges intersecting at the point are used to determine if the point qualifies as a convex point. The internal angle of the point defined by the two edges is calculated. The following calculations are used to calculate the internal angle of a given point.
1. Calculate the angle of the segment from previous point $(x_{i-1}, y_{i-1})$ to $(x_i, y_i)$, and denote this angle as deg1. If i is 1, then use $(x_n, y_n)$ as the previous point.
2. Calculate the angle of the segment from next point $(x_{i+1}, y_{i+i})$ to $(x_i, y_i)$, and denote this angle as deg2. If i is n, then use $(x_1, y_1)$ as the next point.
3. If deg2<deg1, replace deg2 by 2*pi+deg2
4. The internal angle of the vertex is 2*pi−deg2+deg1
5. If the internal angle is less than pi, then this point is a convex vertex; otherwise, it's not a convex vertex.
D. 3 Convert a Polygon to a Convex Polygon
Check every vertex in the given polygon in anti-clock order. If it is not a convex point, remove the point. Repeat the checking for the obtained new set vertices till no more vertex need to be removed. Denote all the points remaining as a set of points, newPts, of length m, where m<=n, and newPts contains a subset of points of Pts in the same order. The point set newPts defines the vertices of a convex polygon.

What is claimed is:
1. A method for identifying a cluster in two-dimensional data in a two-dimensional data space, comprising:
   segmenting, via an apparatus including a processor, said data space into a plurality of radial segments originating at an originating point, wherein said plurality is at least three, and said originating point is in said cluster;
   for each radial segment, generating a radial density histogram;
   determining a cluster boundary from said radial density histogram, to generate a set of cluster boundaries, one for each radial segment; and
   identifying said cluster as consisting of a subset of said data that is enclosed by the set of cluster boundaries.

2. A method for identifying a cluster in two-dimensional data in a two-dimensional data space, comprising:
- segmenting, via an apparatus including a processor, said data space into a plurality of radial segments originating at an originating point, wherein said plurality is at least three, and said originating point is in said cluster; and
- for each radial segment, generating a radial density histogram;
- determining a cluster boundary from said radial density histogram, to generate a set of cluster boundaries, one for each radial segment;
- constructing a polygonal gate surrounding said cluster from said set of cluster boundaries; and
- identifying said cluster as consisting of a subset of said data that is enclosed by said polygonal gate.

3. The method of claim 2, wherein said polygonal gate is a convex polygonal gate.

4. The method of claim 2, wherein said data are obtained using a flow cytometer.

5. A non-transitory computer readable medium comprising instructions executable by a processor of an apparatus, the instructions causing the apparatus to identify a cluster in two-dimensional data in a two-dimensional data space by:
- segmenting said data space into a plurality of radial segments originating at an originating point, wherein said plurality is at least three, and said originating point is in said cluster;
- for each radial segment, generating a radial density histogram;
- determining a cluster boundary from said radial density histogram, to generate a set of cluster boundaries, one for each radial segment; and
- identifying said cluster as consisting of a subset of said data that is enclosed by the set of cluster boundaries.

* * * * *